(12) United States Patent
Manning et al.

(10) Patent No.: US 11,952,603 B2
(45) Date of Patent: Apr. 9, 2024

(54) METHOD FOR REDUCING OR INACTIVATING VIRAL AND MICROBIAL CONTENT IN THE PROCESSES FOR THE MANUFACTURE OF PANCREATIN

(71) Applicants: Kenneth S. Manning, Middleton, WI (US); Yan Wang, Middleton, WI (US); Dustin Nielsen, Santa Barbara, CA (US); Ryan Ruf, De Pere, WI (US); Colin Crowley, Sun Prairie, WI (US); Jon Restivo, Stoughton, WI (US); Dana Spangenberg, Cottage Grove, WI (US); Karla Anhalt, DeForest, WI (US); Mark Romich, New Glarus, WI (US); Anisha Akula, Madison, WI (US); Carmen Fritz, Sun Prairie, WI (US)

(72) Inventors: Kenneth S. Manning, Middleton, WI (US); Yan Wang, Middleton, WI (US); Dustin Nielsen, Santa Barbara, CA (US); Ryan Ruf, De Pere, WI (US); Colin Crowley, Sun Prairie, WI (US); Jon Restivo, Stoughton, WI (US); Dana Spangenberg, Cottage Grove, WI (US); Karla Anhalt, DeForest, WI (US); Mark Romich, New Glarus, WI (US); Anisha Akula, Madison, WI (US); Carmen Fritz, Sun Prairie, WI (US)

(73) Assignee: SCIENTIFIC PROTEIN LABORATORIES, LLC, Waunakee, WI (US)

(*) Notice: Subject to any disclaimer, the term of this patent is extended or adjusted under 35 U.S.C. 154(b) by 1472 days.

(21) Appl. No.: 16/108,930

(22) Filed: Aug. 22, 2018

(65) Prior Publication Data
US 2018/0362958 A1 Dec. 20, 2018

Related U.S. Application Data

(62) Division of application No. 15/159,345, filed on May 19, 2016, now Pat. No. 10,093,916.
(Continued)

(51) Int. Cl.
*C12N 9/92* (2006.01)
*A61K 9/00* (2006.01)
(Continued)

(52) U.S. Cl.
CPC .............. *C12N 9/94* (2013.01); *A61K 9/00* (2013.01); *A61K 31/327* (2013.01); *A61K 35/39* (2013.01);
(Continued)

(58) Field of Classification Search
None
See application file for complete search history.

(56) References Cited

U.S. PATENT DOCUMENTS

| 3,956,483 A | 5/1976 | Lewis |
| 4,986,963 A | 1/1991 | Corcoran et al. |

(Continued)

FOREIGN PATENT DOCUMENTS

| CN | 1516740 A | 7/2004 |
| CN | 101233229 A | 7/2008 |

(Continued)

OTHER PUBLICATIONS

Herzog et al., Pharmazic, 44(3):204-206 (Translation) (1989) (Year: 1989).*
(Continued)

*Primary Examiner* — David W Berke-Schlessel
(74) *Attorney, Agent, or Firm* — Reinhart Boerner Van Deuren P.C.

(57) ABSTRACT

A pancreatin preparation having reduced viral infectivity includes one or more pancreatin enzymes and peracetic acid (PAA). At least one pancreatin enzyme may be derived from an animal source such as a porcine pancreas gland. In a particular embodiment, the one or more pancreatin enzymes
(Continued)

are selected from the group consisting of lipases, proteases, and amylases.

10 Claims, 6 Drawing Sheets

Related U.S. Application Data

(60) Provisional application No. 62/163,779, filed on May 19, 2015.

(51) Int. Cl.
*A61K 31/327* (2006.01)
*A61K 35/39* (2015.01)
*A61K 38/46* (2006.01)
*C12N 7/00* (2006.01)
*C12N 9/94* (2006.01)

(52) U.S. Cl.
CPC .............. *A61K 38/46* (2013.01); *C12N 7/00* (2013.01); *C12N 2750/10063* (2013.01); *C12N 2750/14363* (2013.01); *C12N 2770/32263* (2013.01)

(56) References Cited

U.S. PATENT DOCUMENTS

| | | | |
|---|---|---|---|
| 6,749,851 | B2 | 6/2004 | Mann et al. |
| 2005/0070472 | A1 | 3/2005 | Bronislava et al. |
| 2009/0130063 | A1 | 5/2009 | Becher et al. |
| 2009/0233344 | A1 | 9/2009 | Kurfurst et al. |
| 2011/0268844 | A1 | 11/2011 | Rämsch et al. |
| 2014/0017223 | A1 | 1/2014 | Tijssen et al. |

FOREIGN PATENT DOCUMENTS

| | | |
|---|---|---|
| CN | 101821389 B | 5/2012 |
| CN | 102884181 A | 1/2013 |
| CN | 102939100 A | 2/2013 |
| EP | 2 165 717 A1 | 3/2010 |
| WO | WO 2011/060135 A1 | 4/2011 |

OTHER PUBLICATIONS

Mattle Michael J et al.; "Impact of Virus Aggregation on Inactivation by Peracetic Acid and Implications for Other Disinfectants (vol. 45, p. 7710, 2011)", Environmental Science & Technology, vol. 46, No. 1, Jan. 2012 (Jan. 2012), p. 568, XP002786799.
V Herzog: Possible decontamintation of pancreatin with gamma rays and chemical agents, Pharmazie, vol. 44, No. 3, Mar. 1, 1989 (Mar. 1, 1989), pp. 204-206, XP055526203, DE ISSN: 0031-7144.
Greenspan and Mackeller (1951), The Application of Peracetic Acid Germicidal Washes to Control Mold of Tomatoes (Food Technology 5:95-97).
Kline and Hull (1960), The Virucidal Properties of Peracetic Acid. American Journal of Clinical Pathology 33: 30-33.
Y. Ogata et al. (1972) Oxidation of Vitamin A Alcohol with Peracetic Acid; Tetrahedron vol. 29, pp. 47-50.
Baldry; "The bacterial, fungicidal and sporicidal . . . " ; J. Applied Bacteriology. (1983) 54:417-423.
Cronmiller, J. R., et al. (1999), Efficacy of Conventional Endoscopic Disinfection and Sterilization Methods Against Helicobacter pylori Contamination. Helicobacter 4: 198-203.
Pruss, et al., 1999; "Virus Safety of Avital Bone Tissue Transplants: Evaluation of Sterilization Steps of Spongiosa Cuboids Using a Peracetic Acid-Methanol Mixture". Biologicals 27: 195-201.
Brauniger et al.; "Further studies on thermal resisitance . . . "; Int. J. Hyg. Environ. Health 203, 71-75, 2000.
Soucie et al. "Investigation of porcine parvovirus among persons with hemophilia receiving Hyate:C porcine factor VIII concentrate". Tranfusion (2000) 40:708-711.
Giangrande et al. "Viral pharmacovigilance study of haemophiliacs receiving porcine factor VIII". Haemophilia (2002) 8:798-801.
Hodde and Hiles; "Virus Safety of a Porcine-Derived . . . ", 2002, Biotechnology and Bioengineering 79:211-216.
Fenaux et al. (2004), A Chimeric Porcine Circovirus (PCV) with the Immunogenic Capsid Gene of the Pathogenic PCV Type 2 (PCV2) Cloned into the Genomic Backbone of the Nonpathogenic PCV1 Induces Protective Immunity against PCV2 Infection in Pigs, J. Virology 78: 6297-6303.
Lomas et al.; 'Effects of a peracetic acid . . . ; in Cell and Tissue Banking (2004) 5: 149-160.
Ich Harmonised Tripartite Guideline; Viral Safety Evaluation of Biotechnology Products Derived from Cell Lines of Human or Animal Origin; Q5A(R1), 31 pages; Sep. 23, 1999.
US Department of Health and Human Services, Kathryn C. Zoon , Ph.D., Director; Points to Consider in the Manufacture and Testing of Monoclonal Antibody Products for Human; 50 pages; Feb. 1997.
The European Agency for the Evaluation of Medicinal Products; Note for Guidance on Virus Validation Studies: The Design, Contribution and Interpretation of Studies Validation the Inactivation and Removal of Viruses; 14 pages, London, Feb. 14, 1996.
Eterpi, Mickael et al., 'Virucidal activity of disinfectants against parvoviruses and reference viruses', Applied Biosafety, 2010, vol. 15, No. 4, pp. 165-171.
Park, Eunyoung et al., 'Efficiency of peracetic acid in inactivating bacteria, viruses, and spores in water determined with ATP bioluminescence, quantitative PCR, and culture-based methods', Journal of Water and Health, Mar. 2014, vol. 12, No. 1, pp. 13-23.

\* cited by examiner

Fig. 3

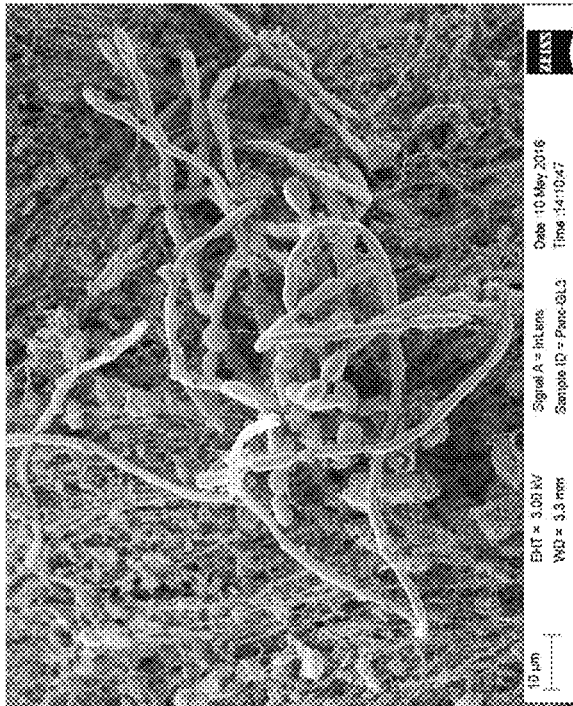
Fig. 4B - non-treated gland tissue showing bacterial colony
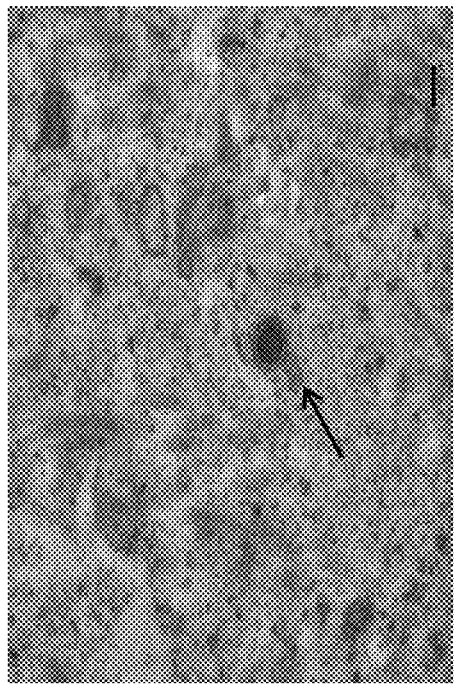
Fig. 4D - non treated pancreatin gland tissue showing virus
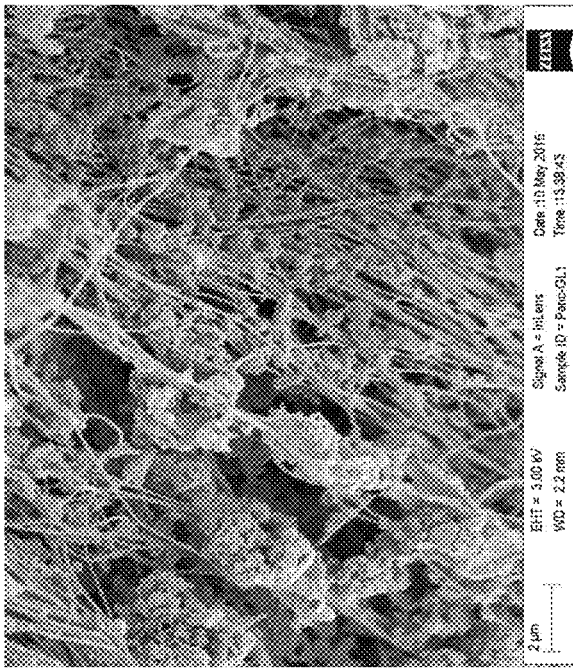
Fig. 4A –PAA treated gland tissue No sign of Bacteria
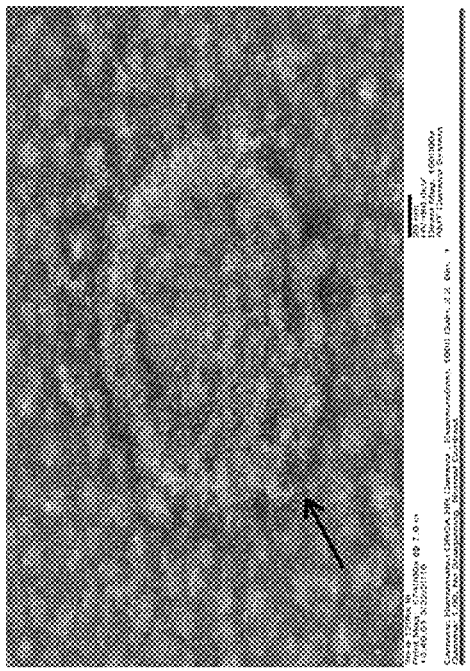
Fig. 4C - non-treated pancreatin powder showing virus

METHOD FOR REDUCING OR INACTIVATING VIRAL AND MICROBIAL CONTENT IN THE PROCESSES FOR THE MANUFACTURE OF PANCREATIN

CROSS-REFERENCE TO RELATED APPLICATION

This patent application is a divisional of U.S. patent application Ser. No. 15/159,345, filed May 19, 2016, which claims the benefit of U.S. Provisional Patent Application No. 62/163,779, filed May 19, 2015, the entire teachings and disclosure of which are incorporated herein by reference thereto.

FIELD OF THE INVENTION

The present invention relates to pancreatin and a method for reducing viral infectivity or inactivating viral and microbial content during processes for the manufacture of pancreatin.

BACKGROUND OF THE INVENTION

Pancreatin is manufactured from porcine pancreatic tissue from animals that have been found suitable for human consumption after veterinary exams. Pancreatin is a mixture of digestive enzymes, mainly amylase, protease and lipase, extracted from porcine pancreas. Due to its important therapeutic properties and high level of safety, pancreatin has long been used as a pharmaceutical preparation in enzyme replacement therapy. A wide variety of pancreatin preparations are commercially available as a digestive enzyme supplement to aid digestion and enhance absorption of nutrients. Clinically, pancreatic enzyme replacement therapy is the mainstay of treatment for pancreatic exocrine insufficiency, which is associated with cystic fibrosis, chronic pancreatitis, post-gastrointestinal bypass surgery, post-pancreatectomy, etc.

A feature common to all biological products obtained from any material of animal or human origin is the risk of viral contamination. Biological contamination may arise either from the source material or from adventitious agents introduced during the manufacturing processes.

Viruses are small infectious agents that replicate only inside the living cells of other organisms. Viruses consist of nucleic acids (RNA or DNA) which are surrounded by a protein shell and in some case, a lipid layer. Viruses producing only a protein shell are commonly known as non-enveloped viruses and those with both protein and lipid components in the shell are commonly known as enveloped viruses. They range in size from about 15 nm to about 450 nm, and cannot be seen with light microscopes. The shape and structure of viruses has been studied by electron microscopy, NMR spectroscopy, and X-ray crystallography.

Viruses can infect all types of life forms, from animals and plants to bacteria and archaea. As viruses cannot replicate independently, they are reliant on hosts. Accordingly they occur in virtually all living things in the world. Very few of the known viruses are pathogenic for humans, as they are highly host specific. Several national authorities have urged pancreatin manufactures to improve the virus inactivation/removal capacities of the manufacturing processes; however, attempts at improvement have met with limited success, due to the fact that most conditions which would remove or inactivate viruses will also result in an inactive product (destroyed enzyme activities). Regulations and safety concerns mandate viral clearance (virus removal or inactivation) in biopharmaceuticals such as pancreatin active pharmaceutical ingredient (API). Consequently, companies producing pharmaceutical products derived from biological tissues are experiencing additional pressure from the regulatory bodies to increase the level of safety of their products by reducing all contaminants to the lowest level possible.

Some small non-enveloped DNA viruses such as porcine parvovirus (PPV) and porcine circovirus (PCV) are difficult to inactivate. Under conditions used to produce the commercial products, the PPV and PCV titers can be reduced but the viruses may not be completely inactivated. However, human infections by exposure to non-enveloped porcine viruses such as PPV and PCV from commercial products have never been reported despite widespread use of these porcine-derived commercial products in humans. For example, PCV DNAs were frequently detected in porcine-derived commercial product such as pepsin and a factor VIII concentrate; however the contaminated products could not elicit any infection when administrated intravenously into pigs [Fenaux et al. (2004), "A Chimeric Porcine Circovirus (PCV) with the Immunogenic Capsid Gene of the Pathogenic PCV Type 2 (PCV2) Cloned into the Genomic Backbone of the Nonpathogenic PCV1 Induces Protective Immunity against PCV2 Infection in Pigs". J. Virology 78: 6297-6303]. PPV DNAs were detected in 21 of the 22 lots of Hyate: C porcine factor VIII concentrate, although serum samples from 98 Hyate: C human recipients all tested negative for PPV antibodies (Soucie et al. "Investigation of porcine parvovirus among persons with hemophilia receiving Hyate: C porcine factor VIII concentrate". Tranfusion (2000) 40:708-711.). Giangrande et al. ("Viral pharmacovigilance study of haemophiliacs receiving porcine factor VIII". Haemophilia (2002) 8:798-801.) also tested serum samples from 81 past recipients of porcine factor III and 125 other volunteers for evidence of antibodies against a range of porcine viruses including PPV, and the results were negative. Therefore, the risk of human infection by PPV, PCV or other non-enveloped porcine viruses that may still be present in commercial product is not supported by published reports, and such a risk, if it exists at all, is extremely small.

The present invention is directed to a method for reducing or inactivating viral and microbial content during a process for the manufacture of pancreatin without compromising purity, composition or potency as measured by enzymatic activity or enzyme activity ratios.

To date no reliable method has been developed for removal or inactivation of all viral contaminants in a pancreatin sample. This is due to the fact that the active enzymes in pancreatin are incompatible with many of the known inactivation conditions including heat, low pH, oxidation and ionizing irradiation. Nonetheless several methods have been published for the inactivation or reduction of viruses and microorganisms.

Tijssen et al (US 2014/0017223 A1) discloses a process for making a pancreatic enzyme preparation (PEP) comprising the step of reacting beta-propiolactone (BPL) with a preparation containing one or more pancreatic enzyme for a sufficient time to reduce a viral infectivity in the preparation.

Rämsch et al. (US patent US 2011/0268844 A1) discloses pancreatin treated with high-pressure and or with a screen filtration followed by a high-pressure treatment of 4000, 5000 or 6000 bar for 5 minutes at 15° C. According to Rämsch, this is applicable to all virus forms, such as DNA and RNA viruses, enveloped and non-enveloped viruses and bacteria and fungi and comprising at least 50% of biological activity. He also further disclosed the unpredictability about whether inactivation of certain viruses using high-pressure treatment is actually successful. Different method condition must be selected depending on whether the samples are liquid or solid owing to the different compressibility of the samples.

Kurfurst, et al. (US 2009/0233344 A1) discloses a method for reducing viral and microbial contamination of a sample by treating the sample with a residual moisture of 0.5 weight % or less, subjecting the pancreatin treated with heat treatment at a temperature of 84° C., preferably 80° C. and below, for 48 hours or 30 hours, wherein the activity of the pancreatin obtained is at least 50% biological activity. The viral infectiousness of the pancreatin is disclosed as reduced by a $\log_{10}$ reduction factor of more than 1 $\log_{10}$.

Mann (US 2009/6749851) discloses methodology for sterilizing preparations of digestive enzymes to reduce the level of active biological contaminants such as viruses, bacteria, yeasts, molds, and fungi. The treatment of compositions comprising digestive enzymes involved stabilizing the compositions by either (a) reducing the temperature of (b) reducing the solvents of, or (c) adding a stabilizer to the composition, followed by irradiation of the composition.

Becher, et al. (US 2009/0130063 A1) discloses a process for separating an infectious viral load from a pancreatin sample for quantitatively determining the viral load in a pancreatin sample using centrifugation and ultra-centrifugation. This method has limitation for only liquid sample suitable for centrifugation.

Braeuniger et al. (Int. J. Hyg. Environ. Health (2000) 203: 71-75) discloses the use of heat for inactivation of the bovine parvovirus (BPV). It has been demonstrated BPV can be deactivated depending upon exposure to heat and residual moisture. However Braeuniger et al did not disclose any effects of heat on enzymatic activity and change in composition.

Lewis (US 1971/3,956,483) discloses a method of pancreatin processing and reduction of bacteria while maintaining the amylolytic, proteolytic and lipolytic activities. The method comprises heating the pancreatin to a sufficiently high temperature between 49-82° C. Lewis, however, fails to provide a process to inactivate or reduce the amount of viruses.

A particular challenge is the inactivation or reduction of viruses from a matrix of biological extracts whose active substance is enzyme mixtures, without destroying or changing the enzymatic activity or ratio of the proteins in the process. There is a demand for methods in which the viral and bacterial content in a biological extract which contains solids is reduced or minimized to the greatest possible extent consistent with preservation of the desired purity, composition and potency of the pharmaceutical active ingredient. The method must be equally suitable for solids and suspensions.

In accordance with ICH Q5A: "*Viral Safety Evaluation of Biotechnology Products Derived from Cell Lines of Human or Animal Origin*", the process developed herein required the reduction or inactivation of viruses from biological products while at the same time needed to maintain enzyme activities and compositional ratios (e.g. lipase, protease and amylase) at an acceptable level. In principle, pharmaceutically active agents should not contain infectious viruses. The current production processes are not able to reduce or inactivate potentially present non-enveloped viruses with a sufficient safety margin, and additional virus-reducing steps must be implemented.

PAA is considered an effective disinfectant that is able to inactivate a wide variety of bacteria (Cronmiller, J. R., et al. (1999), Efficacy of Conventional Endoscopic Disinfection and Sterilization Methods Against *Helicobacter pylori* Contamination. *Helicobacter* 4: 198-203.); fungi (Werner and Wewalka (1973), Oxidation of vitamin A alcohol with peracetic acid. Tetrahedron 29:47-50) and viruses (Kline and Hull (1960), The Virucidal Properties of Peracetic Acid. American Journal of Clinical Pathology 33: 30-33).

Peracetic acid (PAA) has been used also as a germicide in the spraying of fruits and vegetables (Greenspan and MacKeller (1951), "The Application of Peracetic Acid Germicidal Washes to Control Mold of Tomatoes (Food Technology 5:95-97).

Baldry (in J. Applied Bacteriology. (1983) 54:417-423; reported reduction by a factor of $10^6$ in the number of vegetative bacteria within 1 min at 25° C. using a solution containing 1.3 mmol/L of PAA.

Hodde and Hiles (2002, Biotechnology and Bioengineering 79:211-216) demonstrated the use of PAA as a sterilant to inactivate several model viruses from porous, non-crosslinked, collagen-based material used for medical devices. Their work supports the safety of PAA treated materials for human use without fear of viral transmission.

Lomas et al. (in Cell and Tissue Banking (2004) 5: 149-160) reported that treatment of human Bone patellar tendon bone (BPTB) graft with PAA did not render cytotoxic or pro-inflammatory in vitro. BPTB grafts treated with PAA were more susceptible to collagenase degradation. They further described the high-level disinfection protocol, utilizing PAA and its positive effect on the biocompatibility and biomechanics of the patellar tendon allografts.

SUMMARY OF THE INVENTION

The present invention provides a method for reducing or inactivating the microbial and viral contamination of biological extracts, without affecting the activity and without changing the composition of the enzymes contained in the biological extract. Additionally, the method does not produce any toxic compound or residue in the end product.

In one embodiment, a pancreatin preparation is provided. The preparation has a reduced viral infectivity, and includes one or more pancreatin enzymes and PAA. In some embodiments, the preparation includes one or more porcine pancreas glands.

In some embodiments, the pancreatin preparation has a viral infectivity of Encephalomyocarditis virus (EMC) of at least 1 $\log_{10}$ below that of a pancreatin control sample not treated with PAA; a viral infectivity of Murine Minute Virus (MMV) of at least 1 log 10 below that of a pancreatin control sample not treated with PAA; a viral infectivity of Porcine parvovirus (PPV) of at least 1 $\log_{10}$ below that of a pancreatin control sample not treated with PAA, and/or a viral infectivity of non-enveloped viruses of at least 1 $\log_{10}$ below that of a pancreatin control sample not treated with PAA.

In some embodiments, at least one pancreatin enzyme is derived from an animal source.

In other embodiments, one or more pancreatin enzymes are selected from a group consisting of lipases, proteases, and amylases.

In some embodiments, the pancreatin preparation comprises a pancreatin API.

In another embodiment, a pancreatin API derived from a pancreas gland is provided. The pancreatin API has a reduced viral infectivity and a reduced bacterial count. The pancreatin API includes at least 2.0 USP units lipase, at least 25 USP unit protease, and at least 25 USP unit amylase. The pancreas gland is pre-treated with PAA. The pancreatin API has a viral infectivity of PPV, EMC and MMV of at least 1 $\log_{10}$ below that of a pancreatin API control sample not treated with PAA.

In some embodiments, the pancreatin API is in the form of powder.

In some embodiments, the pancreatin API has a viral infectivity of MMV of at least 2 $\log_{10}$ below that of a pancreatin API control sample not treated with PAA. In some embodiments, the pancreatin API has a viral infectivity of MMV between about 2 $\log_{10}$ to about 4 $\log_{10}$ below that of a pancreatin API control sample not treated with PAA.

In another embodiment, a method of manufacturing a pancreatin preparation is provided. The method includes the steps of providing a pancreas gland and reacting the pancreas gland with PAA in a reaction. The reaction with PAA reduces a viral infectivity and reduces a bacterial count in the pancreatin preparation.

In some embodiments, the viral infectivity of non-enveloped viruses in the pancreatin preparation after the reaction is at least 1 $\log_{10}$ lower compared to the viral infectivity of non-enveloped viruses of the pancreatin gland prior to the reaction with PAA.

In some embodiments, the reaction step also includes steps of adding PAA to pancreas gland or tissue, and incubating the pancreas gland or tissue and PAA for a time sufficient to reduce the viral infectivity.

In some embodiments, the reaction comprises PAA at a concentration of about 100 ppm to about 40,000 ppm. In some embodiments, the reaction may comprise PAA at a concentration of about 500 ppm to about 20,000 ppm.

In some embodiments, the reaction is carried out for about 0.5 minutes to about 30 minutes.

In some embodiments, the reaction is carried out at a temperature of about 15° C. to about 22° C.

In some embodiments, the reaction is carried out at a pH of about 1.0 pH to about 5.5 pH.

In some embodiments, the method further includes the step of providing a co-solvent.

The pancreatin and or pancreatic enzymes in any embodiments of the present invention can be derived from an animal source (hog, ox, sheep, porcine, bovine etc.). Pancreatin enzymes include, but are not limited to, lipase, protease and amylase.

BRIEF DESCRIPTION OF THE FIGURES

FIG. 3 show kinetics of MMV inactivation;

FIG. 4A is an electron microscope image of PAA treated gland tissue;

FIG. 4B is an electron microscope image non-treated gland tissue;

FIG. 4C is an electron microscope image of pancreatin powder produced from non-treated gland tissue;

FIG. 4D is an electron microscope image of non-treated gland tissue;

DETAILED DESCRIPTION OF CERTAIN EMBODIMENTS

Figure 1:
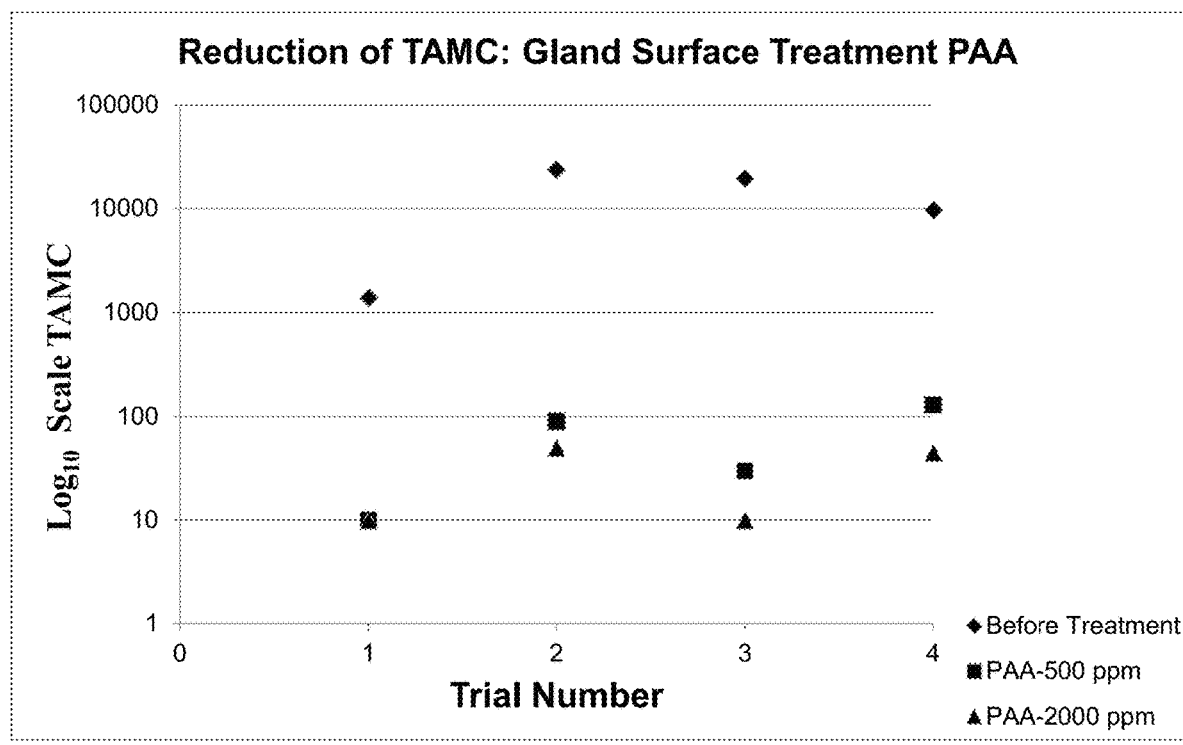
FIG. 1 shows reduction of TAMC in pancreas gland treated with PAA before and after treatment.

The methods described herein comprise treating an animal source of a desired extract, such as a pancreas gland, with a concentration of peracetic acid. Without limitation, the animal pancreas gland can be a bovine or porcine pancreas gland. Advantageously, the resulting pancreatin produced by the methods described herein, as well as the pharmaceutical compositions comprising the pancreatin, may be obtained through laboratory scale, pilot scale and production scale operations.

Peracetic acid treatment (PAA) of pancreas glands: The invention relates to a method of reducing or inactivating viral and microbial content during a process for the manufacture of pancreatin comprising treating an animal pancreas gland, for example a porcine pancreas gland, with a concentration of reagent available for cold sterilization or decontamination such as hydrogen peroxide, percarbonate salts, per benzoic acid, buturic peroxyacid, peracetic acid etc. The method can further comprise providing a pancreatin product, such as a pancreatin API from the treated gland.

The sterilization efficacy of PAA is linked to its rapid penetration into microorganisms and the release of oxygen and free radicals critical for the oxidation and destruction of microbial enzymes. Pruss, et al., (1999; "Virus Safety of Avital Bone Tissue Transplants: Evaluation of Sterilization Steps of Spongiosa Cuboids Using a Peracetic Acid-Methanol Mixture". Biologicals 27: 195-201). Reported titers were reduced by more than 4 $\log_{10}$ when virus-spiked spongiosa cuboids for 4 hours at room temperature (RT) with 1% PAA/24% ethanol (PES) efficiently inactivated most of the viruses tested (human immune-deficiency) virus type 2 (HIV-2), hepatitis A virus (HAV), poliovirus (PV-1), pseudorabies virus (PRV), porcine parvovirus (PPV), and bovine viral diarrhea virus (BVDV), with the exception of HAV. PAA inactivates Gram-positive and Gram negative bacteria, fungi and yeasts in less than 5 minutes at concentrations of <100 ppm. For viruses, the dosage range is wide (100-40,000 ppm).

Peracetic acid (PAA) is an organic compound with the formula $CH_3CO_3H$. This organic peroxide is a colorless liquid with a characteristic acrid odor reminiscent of acetic acid. It is a strong oxidant, can be highly corrosive, and is produced industrially by the autoxidation of acetaldehyde. PAA may be employed in the reactions described herein with or without a co-solvent, such as an alcohol.

According to embodiments of the present invention, animal glands are pre-treated with PAA prior to extraction of a pancreatin API according to methods known to those of skill in the art. Pre-treatment consist of immersing whole animal glands in a solution containing PAA to thereby reduce viral activity and bacterial counts. In other embodiments, pre-treatment may consist of immersing sliced, chopped, or ground animal glands in a solution containing PAA to thereby reduce viral activity and bacterial counts. Pre-treatment of animal glands may be performed at varying concentrations of PAA, temperatures, pH, and lengths of time.

In a preferred embodiment, aqueous solutions having PAA concentrations of between about 100 ppm to 40,000 ppm are employed for pre-treatment. In more preferred embodiments, PAA concentrations of about 500 ppm to about 25,000 ppm are employed. In some embodiments, PAA concentrations of 100-5,000 ppm, 5,000-10,000 ppm, 10,000-20,000 ppm, 20,000-30,000 ppm, 30,000 to 40,000 ppm, or greater than 40,000 ppm may be employed.

In a preferred embodiment, PAA pre-treatment is performed at a pH of between about 1.0 to about 5.5. In a more preferred embodiment, PAA pre-treatment is performed at a pH of between about 2.0 to about 5.0.

In a preferred embodiment, PAA pre-treatment is performed at about room temperature. In some embodiments, PAA pre-treatment is performed at a temperature between about 15° C. and 22° C. In other embodiments, PAA pre-treatment may be performed with a refrigerated solution containing PAA. In such embodiments, PAA pre-treatment may be performed at temperature ranges from just above the freezing point of the aqueous solution to room temperature, for example around 4° C.

In a preferred embodiment, PAA pre-treatment is performed for a duration of about 0.5 minute to about 1 hour. In a more preferred embodiment, PAA pre-treatment is performed for a duration of about 5 minutes to about 30 minutes. In some embodiments, PAA pre-treatment may be performed for 0.5-5 minutes, 5-10 minutes, 10-20 minutes, 30-60 minutes, or more than 60 minutes.

Following PAA pre-treatment, the treated animal glands may be used as a source material for extraction of desired enzymatic products, as is generally known in the art.

In a preferred embodiment, the animal gland is a pancreas gland, and particularly a porcine pancreas gland. Other animal glands, organs, and tissues may also be pre-treated with PAA, including but not limited to lungs, brain, gallbladder, pituitary gland, intestines and intestinal mucus, adrenal gland, bile, and thymus, for use in the manufacture of other animal-derived products, including enzymatic products.

The pre-treatment of animal glands with PAA is especially advantageous because the pre-treatment significantly reduces viral infectivity and bacterial counts on treated glandular material. Unexpectedly, enzymatic products produced from PAA-treated animal glands do not have any significantly alteration of the enzymatic profile of the extracts, as compared to the enzymatic profile of extracts produced by the same processes from animal glands that have not received a PAA pre-treatment.

The term "USP unit" refers to a unit used to measure the potency of an active enzyme present in pancreatin.

One USP Unit of amylase activity is contained in the amount of pancreatin that decomposes starch at an initial rate such that 0.16μ Eq of glycosidic linkage is hydrolyzed per minute under the conditions of the USP Assay for amylase activity.

One USP Unit of lipase activity is contained in the amount of pancreatin that liberates 1.0μ Eq of acid per minute at a pH of 9.0 at 37° C. under the conditions of the Assay for lipase activity.

One USP Unit of protease activity is contained in the amount of pancreatin that under the conditions of the Assay for protease activity hydrolyzes casein at an initial rate such that there is liberated per minute an amount of peptides not precipitated by trichloroacetic acid that gives the same absorbance at 280 nm as 15 nmol of tyrosine.

The viral clearance invention was designed to meet the requirements of CPMP/BWP/268/95. "Note for Guidance on Virus Validation Studies: The Design, Contribution and Interpretation of Studies Validation the Inactivation and Removal of Viruses" CBER/FDA: "Points to Consider in the Characterization of Cell Lines Used to Produce Biologicals", ICH Topic Q5A: "Quality of Biotechnological Products: Viral Safety Evaluation of Biotechnology Products Derived from Cell Lines of Human or Animal Origin" and CBER/FDA: "Points to Consider in the Manufacture and Testing of Monoclonal Antibody Products for Human Use".

The viral clearance invention was conducted in order to establish the capacity and efficiency of the process for the reduction and/or inactivation of viruses that may be present as known or unpredicted contaminants. These experiments were performed by spiking virus and measuring its reduction or inactivation during the subsequent process steps. Viral clearance experiments were conducted in a laboratory equipped for virological work.

Example 1

For the preparation of pancreatin, 3 kg thawed whole porcine pancreas glands and 3 kg of porcine pancreas glands cut into approximately 2-inch strips were submerged in two different concentrations of PAA, 500 ppm and 2000 ppm for 10 and 15 minutes at room temperature (18-22° C.). Treated glands were rinsed with process water and placed into a sterile sample bag and stored at −20° C. for freezing not less than 12 hours. A total of 6 samples were tested per run. The preparation was executed 2 times. The second execution did not include strip glands because it was observed in the first execution that the strip glands became too intractable for further processing.

1. Whole gland (A)—500 ppm;
2. Whole gland (B)—2000 ppm;
3. Strip gland (A)—500 ppm;
4. Strip gland (B)—2000 ppm;
5. Whole gland (C)—No treatment-Control;
6. Strip gland (C)—No treatment-Control. For all result see Tables 1 and 2.

After treatment, glands were processed to obtain pancreatin powder with additional steps of the method of the invention which can comprise: 1) frozen whole pancreas gland and 2-inch strip glands are ground from frozen material; 2) ground material is activated, followed by quenching of activation; 3) separation from insoluble matter; 4) pancreatin precipitation; 5) washing and separation; 6) drying solid residue; 7) milling; and 8) dried non-sterile active pharmaceutical ingredient (API) pancreatin final product is obtained.

The example provided herein was to determine the effect of PAA on whole and 2-inch strip porcine pancreas glands. Both sets of glands were tested for Total Aerobic Microbial Count (TAMC), (reduction in bioburden) as well as viral inactivation before and after PAA treatment. Finished product samples were tested for enzyme activity. For the treated whole glands, the PAA treatment significantly decreased the TAMC (Table 1). The untreated glands had counts of 24,000 and 20,000 CFU/g and after PAA treatment the TAMC results were lowered to between 10 and 90 CFU/g. The same held true for the strips of glands. The untreated strips of glands had a TAMC result of 9,700 CFU/g and the treated glands had decreased counts of 130 and 45 CFU/g. The TAMC results decreased slightly for the whole glands finished product samples. The control samples were 50 and 290 CFU/g. After treatment with 500 ppm and 2000 ppm of PAA, the results ranged from 10 to 25 CFU/g. The strip glands remained consistent. The control sample was <10 CFU/g and treated glands were 30 and 10 CFU/g (Table 2).

TABLE 1

| Sample # | Before Treatment (Control) | After Treatment at 500 ppm | After Treatment at 2000 ppm |
|---|---|---|---|
| Whole Gland TAMC CFU/g Run # 1 | 24,000 | 90 | 50 |
| Whole Gland TAMC CFU/g Run # 2 | 20,000 | 30 | 10 |
| Strip Gland TAMC CFU/g Run # 1 | 9,700 | 130 | 45 |
| Strip Gland TAMC CFU/g Run # 2 | NA | NA | NA |

A relevant analysis in assessing a potential process change is an evaluation for potential enzyme degradation. The data given in Table 1 and 2 demonstrates a lack of significant enzyme degradation at selected concentrations of PPA. FIG. 1 shows a 1 to 2 $\log_{10}$ reduction in TAMC in samples before and after treatment with PAA.

TABLE 2

| Sample # | Protease USP U/mg | Lipase USP U/mg | Amylase USP U/mg | TAMC CFU/g |
|---|---|---|---|---|
| Whole Gland Control Run #1 | 295 | 68 | 549 | 50 |
| Whole Gland Control Run #2 | 304 | 90 | 596 | 29 |
| Whole Gland 500 ppm Run #1 | 282 | 91 | 479 | 25 |
| Whole Gland 500 ppm Run #2 | 301 | 74 | 556 | 10 |
| Whole Gland 2000 ppm Run #1 | 329 | 81 | 585 | 15 |
| Whole Gland 2000 ppm Run #2 | 313 | 76 | 518 | 15 |
| Strip Gland Control Run #1 | 327 | 74 | 540 | <10 |
| Strip Gland 500 ppm Run #1 | 324 | 80 | 564 | 30 |
| Strip Gland 2000 ppm Run #1 | 340 | 74 | 531 | 10 |

Example 2

For the preparation of pancreatin, 3 kg thawed whole glands and 3 kg of milled gland were submerged in two different concentrations of PAA, 500 ppm and 2000 ppm for 10 and 15 minutes at room temperature (18-22° C.). Treated glands were rinsed with purified water and placed into a sterile sample bag and stored at −20° C. for freezing not less than 12 hours. A total of 6 samples were tested per run. The preparation was executed 2 times. Milled glands were difficult to process due to slurry being formed after PAA treatment. The second execution did not include milled glands.
1. Whole gland (A)—500 ppm;
2. Whole gland (B)—2000 ppm;
3. Milled gland (A)—500 ppm;
4. Milled gland (B)—2000 ppm;
5. Whole gland (C)—No treatment-Control;
6. Milled gland (C)—No treatment-Control. For all results see table 3 and 4.

After treatment, glands were processed to obtain pancreatin powder as described in example 1 with additional steps of the method of the invention. The TAMC results for both the whole glands and milled before PAA treatments were similar with 1400 and 1100 CFU/g. After 500 ppm and 2000 ppm PAA treatment, the TAMC results for the treated whole glands were exactly the same, 10 CFU/g. The milled glands were not tested after PAA treatment. See results in table 3.

TABLE 3

| Description # | TAMC CFU/g |
|---|---|
| Whole Gland Before PAA treatment | 1400 |
| Whole Gland After 500 ppm PAA Treatment | 10 |
| Whole Gland After 2000 ppm PAA Treatment | 10 |
| Milled Gland Before PAA Treatment | 1100 |

Figure 6:
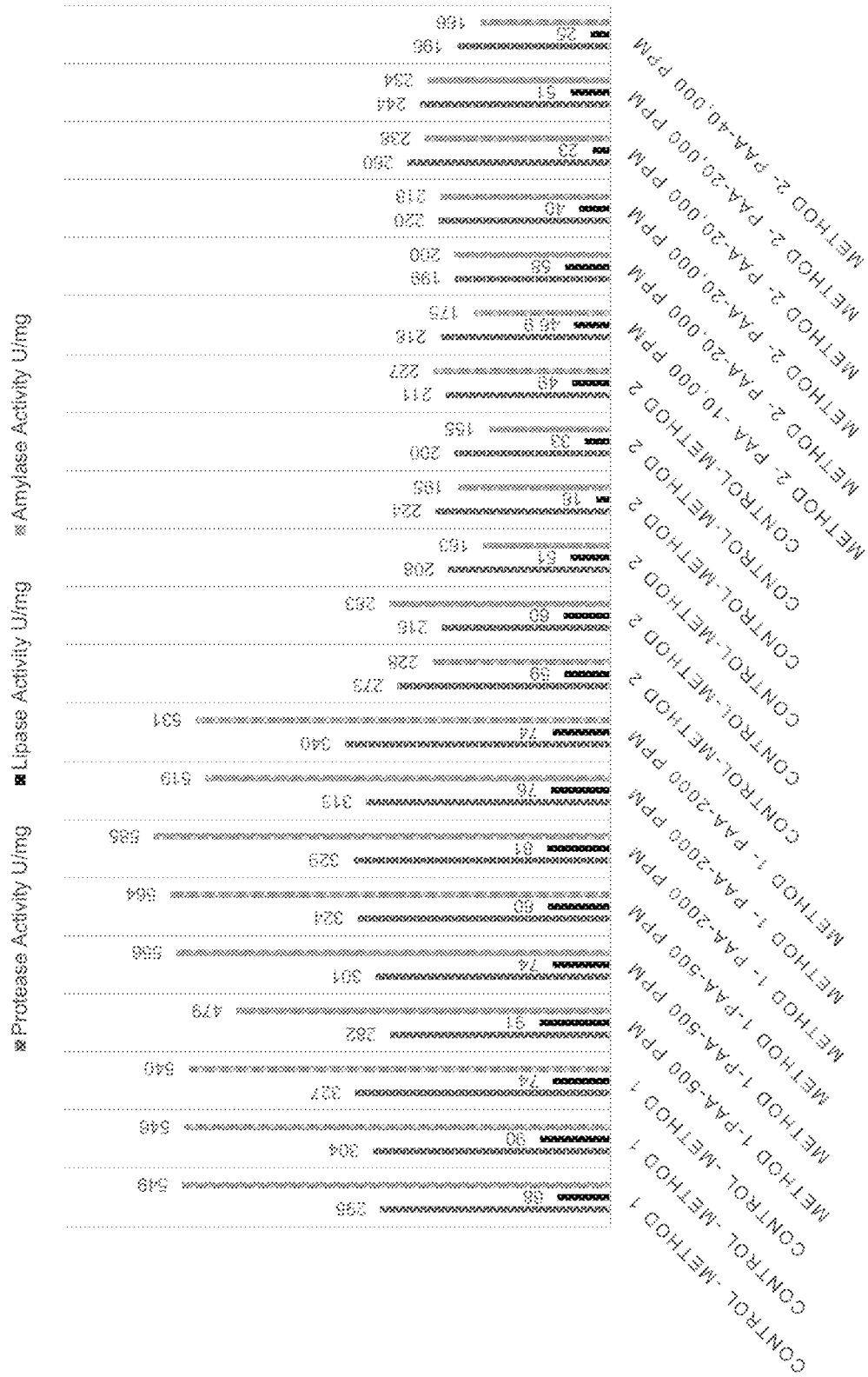
FIG. 6 shows consolidated Enzyme activity with pancreatin samples treated with PAA and non-treated (control).

The enzyme results for whole glands are present in Table 4. The glands subjected to 500 ppm of PAA had the highest enzyme levels. The glands subjected to 2000 ppm of PAA had the next highest levels with the exception of Protease activity which was lower than both the control and the 500 ppm glands. This data is also presented in consolidated FIG. 6

TABLE 4

| Description | Protease USP U/mg | Lipase USP U/mg | Amylase USP U/mg |
|---|---|---|---|
| Whole Gland Control | 400 | 97 | 512 |
| Whole Gland 500 ppm | 407 | 101 | 537 |
| Whole Gland 2000 ppm | 351 | 98 | 526 |

Example 3

Measuring Viral Infectivity Activity: The activity of viruses in the initial and treated pancreatin can be performed by any method known in the art. Preferably, the viral infectivity of one or more viruses is measured in the treated pancreatin. In one embodiment, the viral infectivity of PCV2, PPV and/or other viruses are measured.

In one embodiment, the infectivity assay uses cell cultures growing in tissue culture wells to which samples are applied and infection of the cells are measured.

Pancreatin API samples were manufactured with pancreatin whole gland treated with 500 ppm and 2000 ppm PAA solution following the manufacturing process. The test samples listed in Table 5 were pancreatin API samples dissolved in Dulbecco's Phosphate buffer saline (PBS) with $Mg^{2+}$ and $Ca^{2+}$ to generate a 10% suspension used to determine the titer of infectious Porcine circovirus type 2 (PCV 2) by a cell based in vitro assay using PK-13 cells (porcine kidney cells). The test items analyzed within the interference assay were spiked with 3000 $TCID_{50}$/mL of PCV-2. A final dilution of 1:800 of each solution was used to perform the analyses. The titer was determined by a Large Volume Plating. Furthermore, interfering effects of the test items on PCV-2 infection were evaluated in a comparative endpoint titration assay. The test items did not show negative interfering effects on PCV-2 infection. The results are summarized in table 5.

TABLE 5

| Sample Identification # | PCV-2 titer[$\log_{10}TCID_{50/ml}$] | Negative interfering effect |
|---|---|---|
| Panc. sample 500 ppm | 2.21 | No |
| Panc. sample 2000 ppm | 2.58 | No |
| Panc. sample control | 2.53 | No |
| PCV-2 Reference Std. | 2.97 | NA |

NA—not applicable

Example 4

Figure 2:
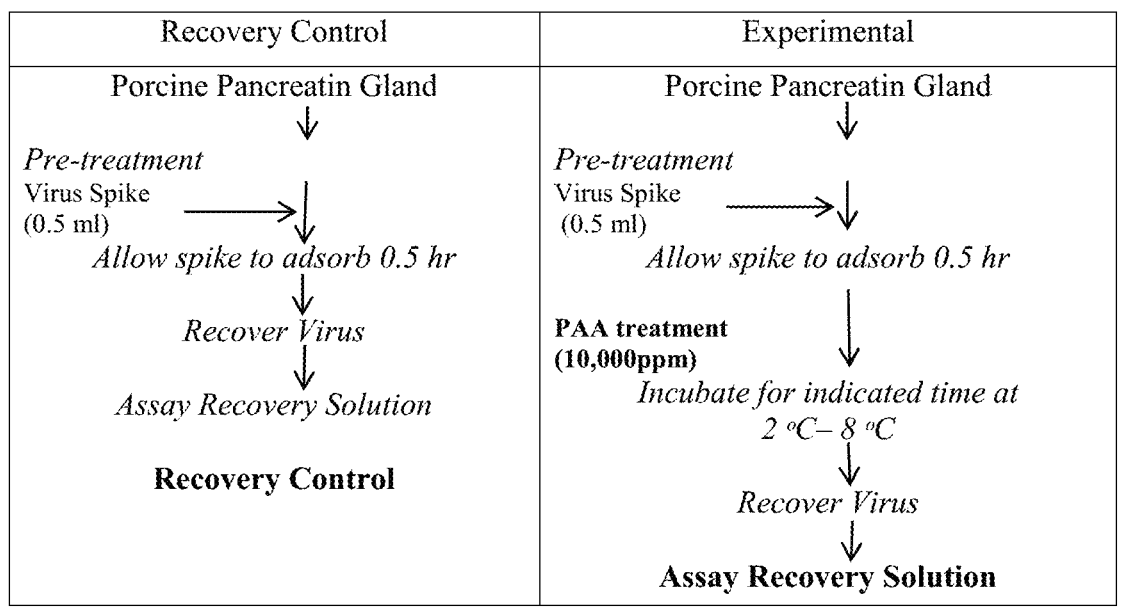
FIG. 2 is a flow chart showing process flow of viruses for infectivity, PAA treatment and exemplary process flow chart.

PAA surface treatment at 500 ppm and 2000 ppm was found to reduce the total count for aerobic microorganisms (TAMC). However, as measured by PCV-2 infectivity test (on endogenous virus) the 500 and 2000 ppm PAA surface treatment has no discernable effect. Therefore an increased concentration of PAA used for surface treatment was tested. The experiment including performance of the process, spiking virus, and treating glands with PAA is detailed in the flow diagram of FIG. 2.

For viral inactivation or reduction experiment with higher concentrations of PAA, the model viruses EMC, MMV and PPV were selected.

EMC is a small non-enveloped virus (20-30 nm) with a RNA genome that belongs to the Picornaviridae family and is icosahedral in structure. It is relatively thermostable, is resistant to organic solvents, non-ionic detergents and is stable at acid pH. This virus is representative of human picornaviruses such as polio virus, hepatitis A virus and rhino virus.

MMV is small non-enveloped virus (18-24 nm) with DNA genome that belongs to the Parvoviridae family and is icosahedral in structure. It is resistant to high temperature, lipid solvents and is stable at acid pH. This virus is considered a severe test of a wide variety of physical and chemical treatments and is a representative model for human parvoviruses and circoviruses that are found at high seroprevalence rates in human populations around the world.

Porcine parvovirus (PPV) is a member of the Parvoviridae family with a single-stranded DNA as genome. PPV is associated with reproductive problems, including abortion, still births, small litters, neonatal deaths and weak piglets. PPV multiplies normally in the intestine of the pig without causing clinical signs. Disease occurs when sero-negative dams are infected in the first half of gestation and the virus crosses the placenta. It is resistant to most disinfectants.

The experiment conducted was to determine if the purification procedures inactivate-viruses as measured by the change in the 50% tissue culture infectious dose ($TDID_{50}$) endpoint assay in the appropriate cell line. The pH of each sample was measured to ensure that the pH was between pH 6-8. Samples were diluted according to the cytotoxicity/viral interference results using assay diluent (EMEM with 2% FBS). The assay method is described in Table 6. Prior to performing the $TDID_{50}$ assay on samples collected, plates were seeded with the appropriate cells. The plates were observed for cytotoxicity prior to inoculation. All control dilution were inoculated 504, per well into 8 replicate wells. All test article dilutions were inoculated in 8 replicate wells.

TABLE 6

| Control/Sample | Description |
| --- | --- |
| Assay Negative Control (all viruses) | Eagle's minimal essential medium (EMEM) with 2% fetal bovine serum (FBS) |
| Assay Positive Control (each virus) | Virus serially diluted 5-fold in EMEM with 2% FBS |
| Test Samples | Serially diluted 5-fold in EMEM with 2% FBS |

The positive control sample gave virus titer±1.0 $log_{10}$ of the certified titer of the virus for each virus on each day of testing confirming the virus in the assay was performing within predetermined specifications. The negative control showed normal morphology and confluence and the absence of viral induced cytopathic effect (CPE) for each virus confirming the detector cell line was performing within predetermined specifications.

When the interference data of PPV virus was analyzed it was determined that there was significant interference at all non-cytotoxic dilutions tested. The undiluted and first dilution (1:5) recovered samples were cytotoxic while the second and third serial dilution (1:25 and 1:125 respectively) recovered samples returned viral titers approximately 1.8 $log_{10}$ below the expected value. The test article is porcine in origin and PPV is a porcine virus. It is most likely the case that the viral interference was due to neutralizing antibodies present in the host. It is unlikely that this type of interference could be relieved by further dilution. The presence of viral interference prevents the accurate measurement of titer, and thus prevents the evaluation of clearance. The portion of the experiment conducted with PPV was terminated.

Figure 3:
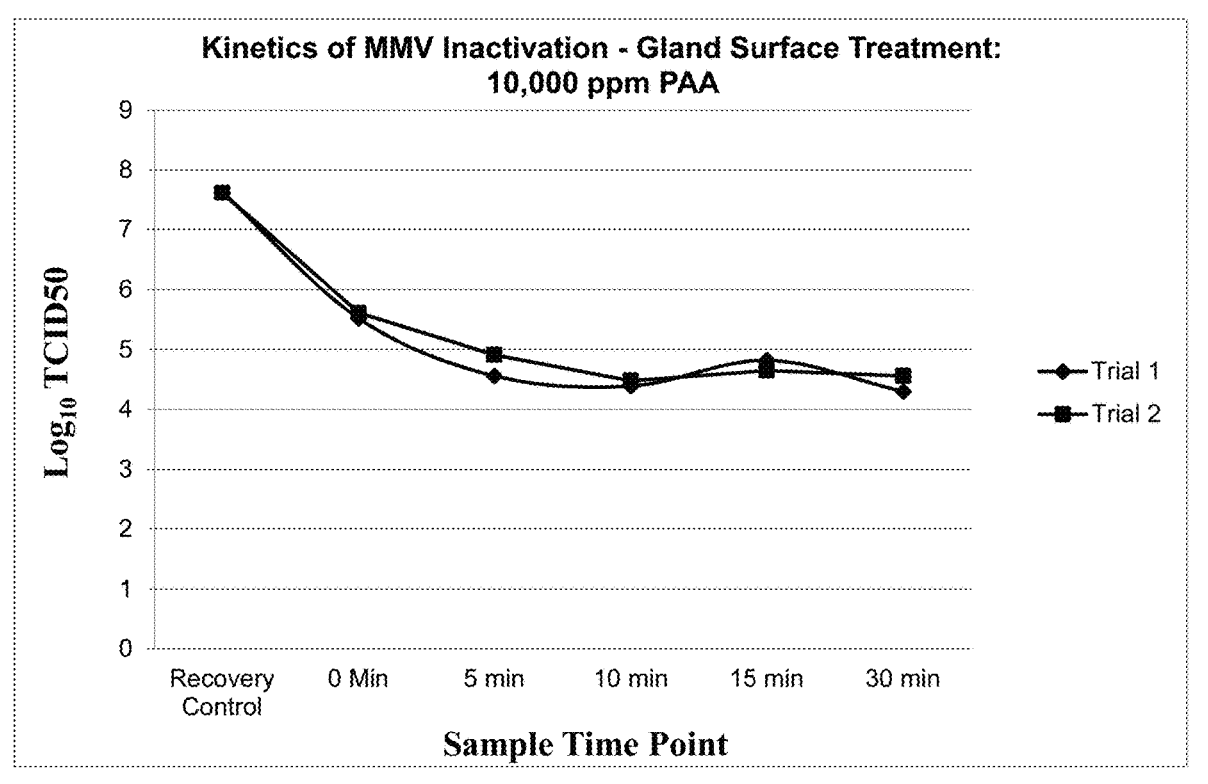

The purification procedure was evaluated for the ability to reduce or inactivate Encephalomycarditis Virus (EMC) and Murine Minute Virus (MMV) spiked into the individual load materials. Clearance was calculated using the Recovery Control, 0 minute sample and 10,000 ppm, 30 minute sample. The test results for EMC showed reduction factor of about 1.75 $log_{10}$ at 15 minutes and about 0.8 $log_{10}$, when calculated using the 30 min sample. MMV test results showed a significant 3.0±0.9 $Log_{10}$ reduction factor, illustrated by the kinetic plot in FIG. 3. Reduction was calculated using the Recovery Control, 0 minute sample and 10,000 ppm 30 min sample.

Example 5

Electron Microscopic Study: Referring to FIGS. 4A-4D, transmission electron microscopy (TEM) and scanning electron microscopy (SEM) were performed to visualize the presence of bacteria and viruses on surface of pancreas gland tissue and pancreatin powder treated with differing concentration of PAA and were compared to non-treated (control) samples.

Pancreas gland tissues treated with PAA and untreated samples as well as resulting pancreatin powder produced with PAA treatment were analyzed with TEM and SEM. For SEM samples were coated with an ultrathin coating of electrically conducting material, deposited on the sample by low-vacuum sputter coating evaporation. A conductive material in current coating used was gold to observe bacteria and viruses. A ZEISS LEO-1530 DSM scanning electron microscope was used to produce the images of FIGS. 4A and 4B. FIG. 4A shows pancreas gland tissue treated with 20,000 ppm PAA for 30 minutes, and shows no sign of bacterial activity. (scale bar is 2 µm). FIG. 4B shows non-treated pancreas gland tissue surface showing presence of abundance bacterial colony (scale bar is 10 µm). Viruses are very small in size (15 to 100 nm) and were not possible to observe in SEM. For TEM the pancreas gland tissue and pancreatin powder sample treated with 20,000 ppm PAA for 30 minutes and control samples were stained with 2% uranyl acetate (aq). A Model H-7600 HITACHI transmission electron microscope, Version 3.01, was used to produces the images of FIGS. 4C and 4D. Three TEM slides of each treatment were observed. Each TEM slide had 400 grids to observe. A minimum of 10-15 grids per slide were observed. Pancreatin control sample (169) did show presence of virus in pancreatin powder and also in pancreatin surface non treated gland tissue. FIG. 4C is a TEM image of a non-treated sample of pancreatin powder (sample 169), showing the presence of virus, indicated by the arrow (scale bar is 20 nm). FIG. 4D is a TEM section of a non-treated surface tissue sample of pancreas gland, showing the presence of virus, indicated by the arrow (scale bar is 200 nm). No virus was found in pancreatin powder sample ID #166, 167 and 168. No virus was observed in pancreatin gland tissue treated with 20,000 ppm PAA for 30 minutes.

Example 6

A method was developed to treat porcine pancreas glands with PAA prior to processing to reduce foreign material and inactivate viruses in a production process without impact on the enzymatic performance of the pancreatin. The goal of this experiment was to demonstrate equivalent enzymatic activity regardless of the presence or absence of pretreatment of the glands. Furthermore, glands that had been treated for viral inactivation demonstrated a reduction in the viral load through the processing and in the final product without impacting enzymatic activity (composition and potency). The viral load of different gland treatments was measured by a different study. This study only measured the enzymatic activity of the glands through the process. This procedure was repeated eight times to fully define the process.

Three treatment conditions were tested in this study. The first treatment condition submerged the glands in a static 10,000 ppm peracetic acid solution at a ratio of 1:1 (wt. glands: wt. PAA solution) for a 5 minute and 30 minute treatment time (sample 163 and 164). The second treatment condition submerged glands in an agitated 20,000 ppm peracetic solution with a ratio of 1:10 (wt. glands: wt. PAA) with the glands secured in a treatment cage and inverted every 5 minutes. The third treatment condition submerged the glands in in an agitated 40,000 ppm peracetic solution with a ratio of 1:10 (wt. glands: wt. PAA) for 30 seconds. The glands were then removed from the peracetic acid solution and the peracetic acid was allowed to react for 30 minutes on the gland surface In all three cases, the glands were rinsed with water and placed in containers and frozen prior to processing for pancreatin extraction.

The glands were then processed and freeze dried. The resulting material was milled to produce pancreatin powder with an average particle size of 180 μm. The pancreatin powder was analyzed for Pancreatin enzyme activities. In process parameters of each of the runs is summarized in Table 7.

Example 7

Figure 5:
FIG. 5 shows a comparison of identification and composition of chromatograms of pancreatin samples treated with different concentration of PAA and pancreatin control samples without PAA treatment.

All samples treated with PAA produced acceptable enzyme activities. The RP-HPLC chromatograms for identification of these samples indicated the proper composition for Pancreatin (see FIG. 5 for a comparison of the chromatograms of the acceptable pancreatin).

The limit test of residual amount of total peroxide was used to check the presence of any remaining PAA in pancreatin API. The limit of detection for this method is 2 ppm in solution, 200 ppm $H_2O_2$ in the sample and 100 ppm total O· (oxygen free radical) in the sample. PAA treatment and rinse samples showed no detection indicating PAA can be removed from pancreatin to less than detection levels.

Based upon these analytical results of the remaining batches, it was that the peracetic acid treatment conditions of the samples did not impact the performance of the final product or the composition, purity, identification and potency.

Example 8

The pancreatin samples were then tested for viral evaluation. The results of these evaluations are summarized in Table 8. All the samples tested negative for specific viral assays and were below the detection limit for the PPV assay. The only sample that demonstrated a difference between the treatments was the PCV2 assay where the samples treated with 20,000 ppm peracetic acid demonstrated lower valves than the other samples although the thawed control sample demonstrated a value equivalent to one of the samples treated with 20,000 ppm peracetic acid. It is unknown whether the bacterial and viral loading of the initial glands were equivalent. However, samples produced from glands treated with 20,000 ppm peracetic acid for 30 minutes demonstrated equivalent or lower PCV2 assay results than any of the other samples.

TABLE 7

| Treatment | Sample ID | Protease (U/mg) | Amylase (U/mg) | Lipase (U/mg) | Fat (%) | LOD (%) | ID test RP-HPLC | Ratio Lipase/ Protease |
|---|---|---|---|---|---|---|---|---|
| Frozen Untreated | 161 | 273 | 228 | 59 | 1.3 | 1.4 | Pass | 0.2161 |
| Thawed Untreated | 162 | 216 | 283 | 60 | 1.5 | 1.2 | Pass | 0.2778 |
| 10,000 ppm PAA/5 minutes | 163 | 256 | 251 | 67 | 1.4 | 2.0 | Pass | 0.2617 |
| 10,000 ppm PAA/30 minutes | 164 | 218 | 175 | 47 | 0.9 | 1.3 | Pass | 0.2151 |
| 20,000 PAA/30 minutes | 166 | 199 | 200 | 58 | 2.5 | 2.2 | Pass | 0.2915 |
| 20,000 PAA/30 minutes | 167 | 244 | 234 | 51 | 0.8 | 1.0 | Pass | 0.2090 |
| 20,000 PAA/5 minutes | 168 | 281 | 278 | 53 | 1.1 | 0.2 | Pass | 0.1886 |
| Control (none) | 169 | 208 | 163 | 51 | 0.8 | 5.4 | Pass | 0.0804 |
| 40,000 PAA/30 minutes | 1614 | 196 | 166 | 25 | 0.8 | 5.7 | Pass | 0.1276 |

TABLE 8

| Treatment | Sample ID | PPV | PCV2 | IFA | VSV | HEV | SVDV | EMCV | PTV | pRota |
|---|---|---|---|---|---|---|---|---|---|---|
| Frozen Untreated | 161 | <2.26 | 2.39 | –ve | –ve | –ve | –ve | –ve | –ve | –ve |
| Thawed Untreated | 162 | <2.26 | 2.26 | –ve | –ve | –ve | –ve | –ve | –ve | –ve |
| 10,000 ppm PAA/5 min | 163 | <2.26 | 2.49 | –ve | –ve | –ve | –ve | –ve | –ve | –ve |
| 10,000 ppm PAA/30 min | 164 | <2.26 | 2.39 | –ve | –ve | –ve | –ve | –ve | –ve | –ve |
| 20,000 ppm PAA/30 min | 166 | <2.26 | 2.26 | –ve | –ve | –ve | –ve | –ve | –ve | –ve |
| 20,000 ppm PAA/30 min | 167 | <2.26 | <2.26 | –ve | –ve | –ve | –ve | –ve | –ve | –ve |
| 20,000 ppm PAA/5 min | 168 | <2.26 | <2.26 | –ve | –ve | –ve | –ve | –ve | –ve | –ve |

–ve = Value Equivalent

Example 9

The resultant glands were then converted into pancreatin using two different proprietary pancreatin extraction processes (designated "Method 1" and "Method 2") were employed, with a product yield of 9-15%. The activities of the pancreatin samples were similar regardless of whether the glands were treated with peracetic acid or not (see Table 7). Treatment conditions up to 40,000 ppm peracetic acid, and submersion times up to 30 minutes, did not impact the activity or potency of the pancreatin produced. Results obtained from pancreatin extraction processes using Method 1 and Method 2 are consolidated and presented in FIG. 6. Furthermore, the reverse phase HPLC identification test results of all the samples were positive for Pancreatin (see FIG. 5).

The viral results indicated that all the samples whether treated with peracetic acid or not tested negative for all the viral panels tested and were below the detection limit for the PPV assay. Samples treated with 20,000 ppm peracetic acid demonstrated equal or lower assay values for the PCV2 assay.

Note that the PPV and PCV2 are not good indicators of viral inactivation efficacy because the study titer of virus is unknown. PCR results are not indicative of viral infectivity.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A pancreatin preparation having reduced viral infectivity comprising one or more pancreatin enzymes and peracetic acid (PAA), wherein an enzymatic profile of the one or more pancreatin enzymes in the pancreatin preparation is the same as it would be if the pancreatin preparation had not been treated with PAA.

2. A pancreatin preparation having reduced viral infectivity comprising one or more pancreatin enzymes and peracetic acid (PAA), further comprising one or more porcine pancreas glands.

3. The pancreatin preparation of claim 1, wherein the pancreatin preparation has a viral infectivity of Encephalomyocarditis virus (EMC) of at least 1 $\log_{10}$ below that of a pancreatin control sample not treated with PAA.

4. The pancreatin preparation of claim 1, wherein the pancreatin preparation has a viral infectivity of Murine Minute Virus (MMV) of at least 1 $\log_{10}$ below that of a pancreatin control sample not treated with PAA.

5. The pancreatin preparation of claim 1, wherein the pancreatin preparation has a viral infectivity of Porcine parvovirus (PPV) of at least 1 $\log_{10}$ below that of a pancreatin control sample not treated with PAA.

6. The pancreatin preparation of claim 1, wherein the pancreatin preparation has a viral infectivity of non-enveloped viruses of at least 1 $\log_{10}$ below that of a pancreatin control sample not treated with PAA.

7. The pancreatin preparation of claim 1, wherein at least one pancreatin enzyme is derived from an animal source.

8. The pancreatin preparation of claim 1, wherein the one or more pancreatin enzymes are selected from a group consisting of lipases, proteases, and amylases.

9. The pancreatin preparation of claim 1, wherein the preparation comprises a pancreatin active pharmaceutical ingredient (API).

10. The pancreatin preparation of claim 7, wherein the one or more pancreatin enzymes are treated with PAA prior to extraction from the animal source.

* * * * *